US00PP07955P

United States Patent [19]

VandenBerg

[11] Patent Number: Plant 7,955

[45] Date of Patent: Aug. 25, 1992

[54] CHRYSANTHEMUM PLANT NAMED YELLOW TRIUMPH

[75] Inventor: Cornelis P. VandenBerg, Salinas, Calif.

[73] Assignee: Yoder Brothers, Inc., Barberton, Ohio

[21] Appl. No.: 599,349

[22] Filed: Oct. 18, 1990

[51] Int. Cl.[5] ..... A01H 5/00

[52] U.S. Cl. ..... Plt./78

[58] Field of Search ..... Plt./78

[56] References Cited

U.S. PATENT DOCUMENTS

PP. 5,995 5/1987 Duffett et al. ..... Plt. 78

4,616,099 10/1986 Sparkes ..... 800/200

*Primary Examiner*—James R. Feyrer

*Attorney, Agent, or Firm*—Foley & Lardner

[57] ABSTRACT

A Chrysanthemum plant named Yellow Triumph particularly characterized by its flat capitulum form; decorative capitulum type; yellow ray floret color; diameter across face of capitulum of 64 to 70 mm. when fully opened; spreading and prolific branching pattern, with 6 to 9 breaks after pinch when grown outside under natural daylength in fall flowering, and 6 to 8 breaks after pinch when grown in 10 cm. pots for spring flowerings; natural season flowering date of Aug. 21 when planting rooted cuttings Jun. 23 in Salinas, Calif., and Sep. 25 when planting rooted cuttings Jun. 15 in Hightstown, N.J.; flowering response of 43 to 46 days after rooting in no light/no shade programs in spring; plant height of 25 cm. when grown in fall under natural daylength with no growth regulators, and 18 to 20 cm. when grown in 10 cm. pots in spring with 0 to 1 applications of 2500 ppm B-9 SP; and durable, uniform performance.

1 Drawing Sheet

The present invention comprises a new and distinct cultivar of Chrysanthemum, botanically known as *Dendranthema grandiflora*, and referred to by the cultivar name Yellow Triumph.

Yellow Triumph, identified as 82-M22C01, is a product of a mutation induction program. The new cultivar was discovered and selected by Cornelis P. VandenBerg on Jul. 20, 1987 in a controlled environment in Salinas, Calif., as one flowering plant within a flowering block established as rooted cuttings from stock plants which had been exposed as unrooted cuttings to an X-ray source of 1750 rads. The irradiated parent cultivar was Triumph, a flat decorative spray pot mum and garden mum in the bronze category, although its ray florets are yellow-orange. Triumph is disclosed in U.S. Plant Pat. No. 5,995.

With more specific reference to the mutation induction program resulting in the selection of Yellow Triumph, three separate groups of rooted cuttings were irradiated on Jan. 8, Jan. 22 and Feb. 5, 1987 at levels of 2000, 1750 and 1500 rads, respectively. Thereafter, 129 of the plants irradiated at 2000 rads were planted Apr. 20, 1987; 446 plants irradiated at 1750 rads were planted May 11, 1987; and 577 plants irradiated at 1500 rads were planted May 25, 1987. All plants were allowed to flower, and 31 original selections were made. Of these, all were eventually discarded except for Yellow Triumph which was, as noted, selected Jul. 20, 1987, and the cultivar Dark Triumph, selected on the same day. Dark Triumph was a selection from the plants irradiated at 1500 rads. A plant patent application of applicant for Dark Triumph is pending. Both the ray floret and flower center of Dark Triumph are substantially darker in color than the flower color of Triumph, and completely dissimilar to the bright yellow ray floret color of Yellow Triumph.

The first act of asexual reproduction of Yellow Triumph was accomplished when vegetative cuttings were taken from the initial selection in Sep. 1987 in a controlled environment in Salinas, Calif., by technicians working under the supervision of Cornelis P. VandenBerg.

Horticultural examination of controlled flowerings of successive plantings has shown that the unique combination of characteristics as herein disclosed for Yellow Triumph are firmly fixed and are retained through successive generations of asexual reproduction.

Yellow Triumph has not been observed under all possible environmental conditions. The phenotype may vary significantly with variations in environment such as temperature, light intensity and daylength.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Yellow Triumph, which, in combination, distinguish this Chrysanthemum as a new and distinct cultivar:

1. Flat capitulum form.
2. Decorative capitulum type.
3. Yellow ray floret color.
4. Diameter across face of capitulum of 64 to 70 mm. when fully opened.
5. Branching pattern is spreading and prolific, with 6 to 9 breaks after pinch when grown outside under natural daylength in fall flowerings, and 6 to 8 breaks after pinch when grown in 10 cm. pots for spring flowerings.

1

6. Natural season flower date of Aug. 21 when planting rooted cuttings on Jun. 23 in Salinas, Calif., and Sep.

25 when planting rooted cuttings Jun. 15 in Hightstown, N.J.

7. Flowering response of 43 to 46 days after rooting in no light/no shade programs in spring.

8. Plant height of 25 cm. when grown in fall under natural daylength with no growth regulators, and 18 to 20 cm. when grown in 10 cm. pots in spring with 0 to 1 applications of 2500 ppm B-9 SP.

9. Durable, uniform performance.

The accompanying photographic drawing is a color photograph of Yellow Triumph grown as a pinched pot mum with four cuttings in a 15 cm. pot, with the colors being as nearly true as possible with illustrations of this type.

Of the commercial cultivars known to the inventor, the most similar in comparison to Yellow Triumph is the parent cultivar Triumph. Most major traits of Yellow Triumph are similar to those of Triumph, except for the following. The ray floret color of Yellow Triumph is a bright, intense yellow, while the ray floret color of Triumph is a yellow-orange (with dark center) classified in the bronze category. In addition, Yellow Triumph has several more disc florets than Triumph, a slightly earlier flowering response in fall flowerings by 1 to 4 days, and a slightly shorter plant height by 2.5 to 5 cm.

In the following description color references are made to The Royal Horicultural Society Colour Chart. The color values were determined on plant material grown as a pinched spray pot mum in Salinas, Calif. on May 3, 1990.

Classification:

*Botanical.*—*Dendranthema grandiflora* cv Yellow Triumph.

*Commercial.*—Flat decorative spray pot mum and garden mum.

INFLORESCENCE

A. Capitulum:

*Form.*—Flat.

*Type.*—Decorative.

*Diameter across face.*—64 to 70 mm. when fully opened.

B. Corolla of ray florets:

*Color (general tonality from a distance of three meters).*—Yellow.

*Color (upper surface).*—12A.

*Color (under surface).*—9A.

*Shape.*—Flat, straight, very slightly ribbed.

C. Corolla of disc florets:

*Color (mature).*—14A.

*Color (immature).*—145B.

D. Reproductive organs:

*Androecium.*—Present on disc florets only; few disc florets present.

*Gynoecium.*—Present on both ray and disc florets.

PLANT

A. General appearance:

*Height.*—25 cm. when grown in fall under natural daylength with no growth regulators, and 18 to 20 cm. when grown in 10 cm. pots in spring with 0 to 1 applications of 2500 ppm B-9 SP.

*Branching pattern.*—Spreading and prolific, with 6 to 9 breaks after pinch when grown outside under natural daylength in fall flowerings, and 6 to 8 breaks after pinch when grown in 10 cm. pots for spring flowerings.

B. Foliage:

*Color (upper surface).*—147A.

*Color (under surface).*—147B.

*Shape.*—Small, lobed.

I claim:

1. A new and distinct Chrysanthemum plant named Yellow Triumph, as described and illustrated.

* * * * *

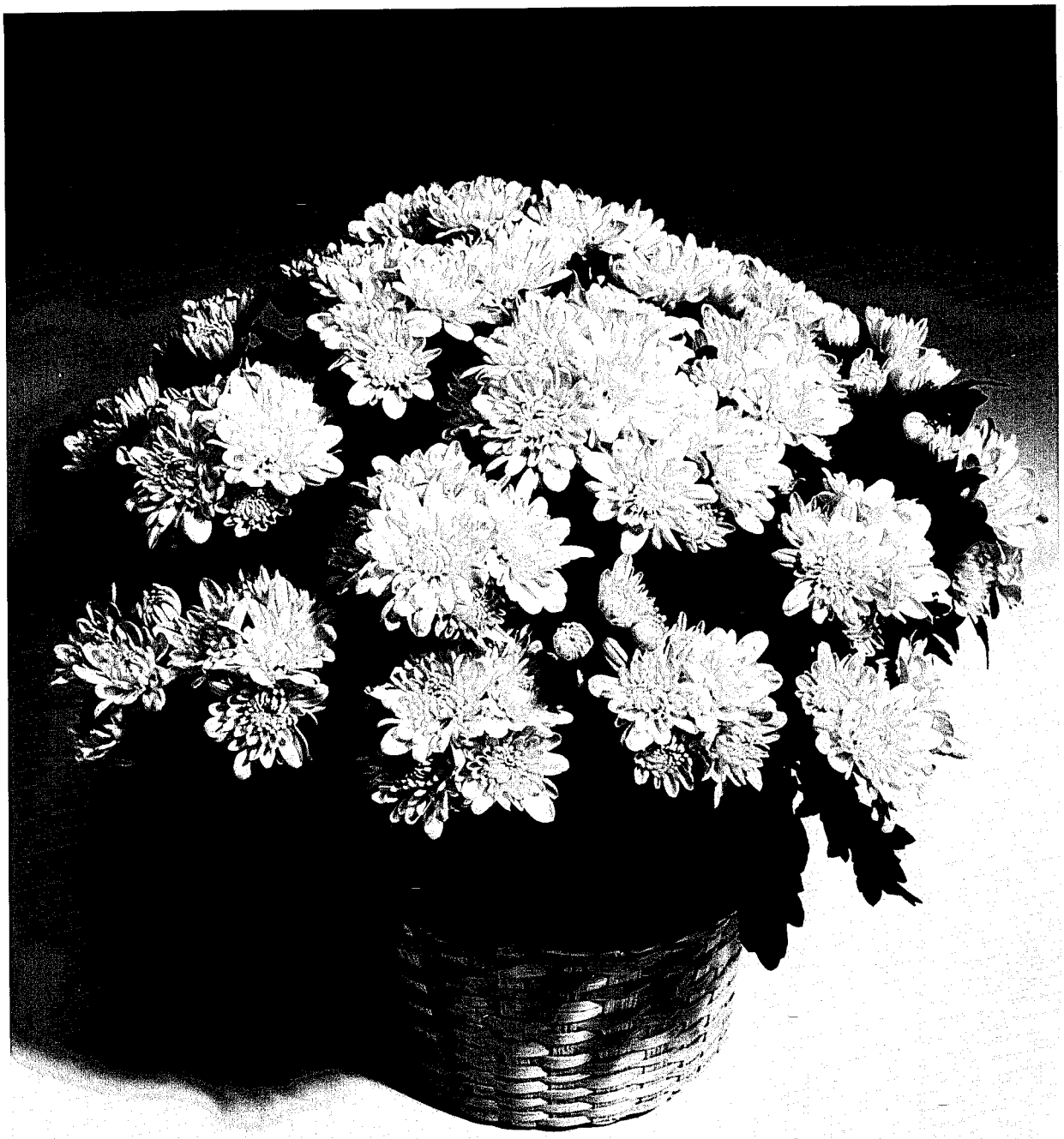

UNITED STATES PATENT AND TRADEMARK OFFICE

CERTIFICATE OF CORRECTION

PATENT NO. : PP 7,955

DATED : August 25, 1992

INVENTOR(S) : Cornelis P. VANDENBERG

It is certified that error appears in the above-identified patent and that said Letters Patent is hereby corrected as shown below:

Column 1, line 18, "rooted cuttings" should read --unrooted cuttings--.

Signed and Sealed this

Second Day of November, 1993

Bruce Lehman

*Attest:*

BRUCE LEHMAN

*Attesting Officer*

*Commissioner of Patents and Trademarks*